United States Patent [19]

Sugarbaker

[11] Patent Number: 5,336,171
[45] Date of Patent: Aug. 9, 1994

[54] ABDOMINO-PELVIC LAVAGE APPARATUS AND METHOD

[76] Inventor: Paul H. Sugarbaker, 3629 Fulton St. NW., Washington, D.C. 20007

[21] Appl. No.: 163,552

[22] Filed: Dec. 9, 1993

[51] Int. Cl.⁵ .......................................... A61M 37/00
[52] U.S. Cl. ........................................ 604/24; 604/23
[58] Field of Search ................. 604/23, 24, 26, 29, 604/30, 104, 289, 304, 305; 128/205.26, 202.12, 205.22, 802; 600/21

[56] References Cited

U.S. PATENT DOCUMENTS

| | | | |
|---|---|---|---|
| 4,328,799 | 5/1982 | Lo Piano | 128/205.26 |
| 4,474,571 | 10/1984 | Laslay | 604/23 |
| 4,612,916 | 9/1986 | Akers et al. | 600/21 |
| 4,624,656 | 11/1986 | Clark et al. | 604/23 |
| 4,801,291 | 1/1989 | Loori | 604/23 |

*Primary Examiner*—C. Fred Rosenbaum
*Assistant Examiner*—Manuel Mendez
*Attorney, Agent, or Firm*—Nath, Amberly & Assoc.

[57] ABSTRACT

An abdomino-pelvic lavage apparatus adapted to be secured in a midline abdominal incision to form a well with the abdomino-pelvic cavity for lavaging the abdomino-pelvic cavity during surgery. The apparatus includes a cylindrical wall made of a transparent plastic material and having structure at its base end for securing the wall in place and effecting a water-tight seal with the edge of an abdominal incision. Ports through the wall around its circumference provide openings for the surgeon's hands so that the surgeon has free access to the abdomino-pelvic cavity for manipulation of intra-abdominal tissues, lavage fluid and inflow and outflow tubes for the lavage fluid. A transparent removable cover may be placed on the wall during chemotherapy treatment to contain fumes and prevent spillage, and to permit pressurization of the well and abdomino-pelvic cavity. Inflow tubes extend through the wall to admit lavage fluid and pressurized gas into the abdomino-pelvic cavity, and outflow tubes drain the lavage fluid from the cavity. Heat sensors, pH monitors, and a pressure gauge on the apparatus, and associated Geiger counters permit accurate monitoring and control of these parameters in the abdomino-pelvic cavity during the procedure. Fluid from drain sites may be sampled for desired data during the lavage procedure.

29 Claims, 8 Drawing Sheets

ABDOMINO-PELVIC LAVAGE APPARATUS AND METHOD

FIELD OF THE INVENTION

This invention relates generally to surgical appliances, and more particularly to an apparatus and method for lavaging the abdomino-pelvic area during or after surgery.

DESCRIPTION OF THE PRIOR ART

One of the signs of the dissemination of gastrointestinal and gynecologic cancers is the peritoneal dissemination of the disease. Most patients with severe peritoneal dissemination of cancer die within one year. In an attempt to improve the control of intra-abdominal cancer, large doses of anti-cancer drugs may be injected into the peritoneal cavity. This therapy has shown marginal effects, and other therapies have been developed in an effort to better control the peritoneal dissemination of cancer.

It has been observed that hyperthermia seems to have a direct anti-cancer effect and synergy with some kinds of anti-cancer drugs, so that the toxicity for cancer cells is significantly increased at an elevated temperature. Accordingly, hyperthermic peritoneal lavage with a chemotherapy solution has been utilized to wash away free cancer cells in the peritoneal cavity by irrigation with massive perfusate, to kill cancer cells by hyperthermia, and to kill cancer cells by the direct effects of chemotherapy.

Conventional techniques employing hyperthermic peritoneal lavage rely upon the use of a tube for infusion of heated fluid into the peritoneal cavity, and one or more drain tubes for removing the perfusate from the cavity. These tubes may be inserted through small stab incisions formed in the wall of the abdomen and guided by the surgeon into the general vicinity of the area it is desired to irrigate, or the surgeon may make a larger incision and visually place the tubes for appropriate irrigation of the peritoneal cavity. Direct manipulation of the tubes and the viscera during perfusion of the abdomino-pelvic cavity is impossible with conventional techniques.

Further, temperature is typically monitored on the inflow and outflow tubes but not in the peritoneal cavity itself, thereby reducing the accuracy of control over temperature and consequently reducing the effectiveness of the hyperthermic treatment.

The effectiveness of abdomino-pelvic perfusion using conventional techniques is further reduced because the heating effects of hot water may not reach cancer cells in the deep areas of the peritoneum or mesenterium, but only washes away floating cancer cells in the peritoneal cavity.

Moreover, assessment of the efficacy of this procedure by measuring the ascites volume by computer tomography or ultra-sonography or the cytologic examination of ascites does not necessarily reveal residual or recurrent cancer in the peritoneal cavity.

There are limited diagnostic methods available to establish the occurrence of peritoneal dissemination of cancer. In most patients, this pattern of dissemination is seen at the time of surgical removal of the primary gastrointestinal or ovarian cancer. In some patients, the peritoneal recurrence of cancer is imaged by abdominal computerized tomography. In other patients, the rise in a tumor marker may lead to the diagnosis of peritoneal dissemination. In some situations, a second look operation is the only reliable procedure to assess the disease state of the cancer patient.

The second look operation (SLO) was introduced into gastrointestinal surgery to provide the surgeon with a means for assessing the status of the disease approximately one year after the initial operation, before advanced disease has occurred and before the reactivation of symptoms. In gynecology, especially, SLO has been gradually approved as a useful means for assessing tumor response, removing recurrent cancer, and planning subsequent treatment in the follow-up of patients with ovarian cancer.

In order to overcome at least some of the shortcomings of prior techniques, while at the same time taking advantage of the beneficial effect of hyperthermia in cancer therapies, Takashi Fujimura, et al. *Continuous Hyperthermic Peritoneal Perfusion for the Treatment of Peritoneal Dissemination in Gastric Cancers and Subsequent Second-Look Operation*, Takashi Fujimura, MD, Yutaka Yonemura, MD, Sachio Fushida, MD, Masaaki Urade, MD, Shigeru Takegawa, MD, Toru Kamata, MD, Kazuo Sugiyama, MD, Hajime Hasegawa, MD, Kanji Katayama, MD, Koichi Miwa, MD, and Itso Miyazaki, MD. Cancer 65:65-71, 1990, have developed a method and apparatus for continuous hyperthermic peritoneal perfusion in combination with the administration of anti-cancer drugs having synergism with hyperthermia.

The apparatus developed by Fujimura, et al., comprises an acrylic cylinder with a flange at each end. One of the flanges is hung on the abdominal wall and the other is suspended from two right-angled bars fixed to the operating table. The cylinder is open-ended and is fixed in the wound made by the surgeon. It is large enough to permit the small intestine to float in the perfusate and the heated saline infused into the peritoneal cavity. Tubes extended into the peritoneal cavity through the cylinder are used to introduce and remove lavage fluid from the cavity.

Although the Fujimura, et al., apparatus solves some of the problems of prior art systems and techniques, it is intended for use only in the operating room while the lavage procedure is being performed. Further, in this apparatus one set of flanges at one end of the cylinder mount on the wound and the other set of flanges at the other end of the cylinder are hung from bars carried by the operating table. Also, the surgeon must gain access to the abdominal cavity through the open top of the cylinder, and the infeed and outflow tubes for the lavage fluid also generally pass through the open top.

Accordingly, there is need for an abdomino-pelvic lavage apparatus which has means for simple and secure water-tight mounting on the wound through the abdominal wall, and which has couplings for quick and easy mounting of inflow and outflow tubes and pressure and temperature monitors on the wall of the appliance. There is also need for such an apparatus which may be left in place after the patient leaves the operating room, whereby follow-up examinations and treatment may be performed in a surgical intensive care unit (SICU) without necessitating a further operation or even requiring use of the operating room. It would also be desirable to seal the open top of the appliance so that chemotherapy could be performed without danger of exposure of operating room personnel to chemotherapy aerosols. Moreover, a desired feature would be openings in the side wall for free access of the surgeon's hands to the peritoneal cavity. Another desired feature would be an adjustable side wall to permit the apparatus to be elongated or otherwise adjusted to different size abdominal incisions.

DESCRIPTION OF THE INVENTION

The invention comprises an apparatus for irrigating the abdomino-pelvic cavity during or after surgery. More particularly, the invention relates to an abdomino-pelvic lavage apparatus for peritoneal lavage in the treatment of diseases disseminated through the peritoneal cavity, and especially in the hyperthermic treatment of the peritoneal dissemination of gastrointestinal, ovarian and other intra-abdominal cancers. The invention especially allows the use of pressure and heat, coupled with manipulation of the organs, in peritoneal lavage procedures.

The apparatus is adapted to be secured in the midline abdominal incision, and comprises an open-ended cylindrical wall having an upper end projecting above the abdominal wall and a base end with means for securing and sealing in a water-tight manner the apparatus in the incision to form a well for containing the lavage fluid used to treat the surfaces of the abdomen and pelvis. For gastrointestinal and gynecologic cancer patients, this includes all sites at risk for local recurrence and peritoneal seeding. Heated lavage fluid under pressure with anti-cancer drugs are added until the abdominal and pelvic cavities are completely filled with the fluid.

Ports along the wall provide passage for inflow and outflow tubes for the lavage fluid, and for temperature sensing devices extended into the abdominal cavity.

Additional ports permit the surgeon to have free access to the abdominal cavity for selective positioning of the inflow and outflow tubes and temperature sensing devices, and for manipulation of the intra-abdominal organs so that all fibrinous accumulations that may harbor cancer cells are disbursed. In cancer patients this allows manual "scrubbing" of the narrow margins of the excision, manipulation of all peritoneal crevices, and visual inspection of all bowel surfaces.

Further ports provide for the introduction of a pressurized gas to place the lavage fluid and anti-cancer drugs under pressure for forcing the drug into tissues which are at great risk, and to ensure that the lavage fluid and drug reach relatively remote and inaccessible areas.

Still further ports provide for pH monitoring, drug monitoring and sampling of the lavage fluid for other laboratory tests.

A cover is secured over the upper end of the wall to confine aerosols and make the operating room environment safe for operating room personnel during chemotherapy.

The lavage fluid may contain acid to lower pH, sugar to elevate glucose levels, antibiotics, chemotherapy (using multiple agents) and fibrinolytic agents, and should be exchanged every ten to fifteen minutes to irrigate away cancer cells, fibrinous debris and other intra-abdominal contaminants. it may be heated and circulated by use of a hater and peristaltic pump such as found in a conventional heart-lung machine, with a single inflow tube for supplying the lavage fluid to the abdominal cavity and one, two, three or more drain tubes for draining the lavage fluid from the abdominal cavity. One drain tube should be placed beneath the right hemidiaphragm, one beneath the left hemidiaphragm and the other in the abdomino-pelvic cavity. The drain tubes should be moderately stiff, with multiple side openings, and a heat sensor should be associated with the distal end of each for monitoring the temperature of the lavage fluid, in situ, throughout the procedure. A pH monitor and pressure sensor are also provided to monitor the pH and pressure of the lavage fluid. Other data may be collected through ports, as desired, such as glucose level, chemotherapy level, etc.

Sampling of the lavage fluid drained from the abdominal cavity is performed regularly throughout the procedure so that the absorption of chemotherapy can be ascertained, and a geiger counter may be located over the abdomen so that any absorption from the abdomen into the systemic circulation can be estimated. This is accomplished with the use of radioactive technetium, which may or may not be attached to various molecules such as albumin. A counter over the heart enables the amount of absorption from the abdomino-pelvic cavity to be documented in an on-line manner. Simultaneous readings in the abdominal cavity and over the heart will enable the absorption of chemotherapy to be estimated and a maximum systemic dosage of drug delivered with the surgical event.

The cylindrical wall is preferably made of a lightweight but strong, clear plastic material, such as Ultem ™, made by General Electric Company, with an oval shape in transverse cross-section. It and other components of the apparatus may be made disposable if desired. To facilitate disposal of the used cylinder, it may be scored at intervals to define fracture lines. Consequently, the used cylinder may simply be stepped on to cause it to fracture along the fracture lines into smaller components for easier disposal. Absorption of potent chemotherapy drugs into the plastic material make cleaning and storage potentially hazardous.

Additionally, the cylinder may be made in several different sizes, or made adjustable so that it will fit all large abdominal incisions.

To secure and seal the cylinder in place in an abdominal incision, several alternate structures are provided. The simplest is an annular skirt that is attached to an outer surface of the cylinder above its base end. In use, the base end of the cylinder is placed in the abdominal incision and the skirt stitched to the abdominal wall above the wound. This form of the invention would be used, for example, when it is not intended or desired to pressurize the abdominal cavity. In another form of the invention, an inflatable annular ring may be provided between two spaced, parallel flanges on the base end of the cylinder. After the edge of the incision has been placed between the flanges, the ring is inflated to securely grip and effect an air and water-tight seal with the abdominal wall at the edge of the incision. Alternatively, a compression plate with screws to fix the cylinder to the edges of the abdominal incision may be utilized. A saw tooth surface is used to maintain the abdominal wall between the compression plates despite abdominal pressure.

An irrigation procedure using the invention may be performed in two stages for cancer patients, i.e., one hour of irrigation with a fibrinolytic agent, performed with the abdominal well open to atmosphere, during which all debris, cancer cells and fibrinous material will be flushed from the peritoneal cavity. This preliminary lavage also provides a thorough test for leakage of fluid from the abdomino-pelvic cavity. Following the initial irrigation, the cover is placed on top of the cylindrical wall and all fibrinolytic phase fluid is removed from the abdomino-pelvic cavity. A pressurized irrigation with heated chemotherapy is then conducted for approximately one hour, after which the chemotherapy fluid is removed and the abdomino-pelvic cavity rinsed. Following the rinse, the surgeon is free to re-enter the abdominal cavity with a greatly reduced risk of exposure of operating room personnel to chemotherapy drugs. At this time, all reconstructive procedures, such as bowel anastomoses, are performed.

In some patients, a particular portion of the abdomino-pelvic cavity will be at increased risk for cancer recurrence. This is true, for example, in a patient with rectal cancer with pelvic recurrence. In this instance, the surgeon may wish to treat a particular portion of the abdominal cavity with an especially high dosage of chemotherapy. It may further be desired to place this chemotherapy under pressure. In these cases, the operating room table may be adjusted to incline the patient's body so that the pelvis is lower and can be filled with high concentration of multi-drug chemotherapy. A temperature probe, inflow tube and outflow drain are placed in this "puddle" of chemotherapy. In this special clinical situation, the inflow and outflow catheters are placed in a single portion of the abdomen, such as the pelvis. While the pelvis is filled and refilled with heated chemotherapy, pressure is applied up to 100 mm. of water in order to force the chemotherapy into the tissues which are at great risk. After this "boost" dose of chemotherapy to the area at great risk, additional lavage fluid is added and the remainder of the abdominal cavity at less risk is treated with a lower dose of chemotherapy, heat and pressure. The exact dose of chemotherapy still present in the intra-abdominal "puddle" can be estimated from the on-line readout of activity within the pelvis as compared to the activity that is noted by readout of radioactive counts over the heart.

The abdomino-pelvic lavage apparatus of the invention may have uses other than in oncology. For instance, it could be used for treatment of patients with intra-abdominal sepsis by irrigating the abdominal cavity with antibiotic and fibrinolytic agents. In this way, all of the infected fibrin could be removed from the abdominal cavity. Heat and detergent could also be used to dislodge the bacteria, whereby bacterial counts could be brought down to an extremely low level by the repeated irrigation of the abdominal cavity. The additional time that the lavage fluid is present in the abdominal cavity by use of the invention would be of great value in eliminating sources of bacterial or fungus infection. Moreover, the fact that the antibiotic can be given under pressure when using the apparatus of the invention would tend to move high concentration of antibiotic rapidly into the surface tissues. With the removal of all contaminated fibrinous material, the patient would be expected to improve more quickly from surgery.

In patients with disease states like pancreatitis, it would be expected that the patient would not need to return to the operating room on numerous occasions in order to ensure that no sepsis remained, as is utilized in the "zipper" technique. The patient would merely be transferred to an ICU setting with the apparatus in place. Repeated inspection and lavage of the abdominal cavity could be accomplished without return to the operating room. Only when the abdominal or pelvic sepsis had resolved would surgical repair of the abdominal incision in the operating room be required.

BRIEF DESCRIPTION OF THE DRAWINGS

The foregoing as well as other objects and advantages of the invention will become apparent from the following detailed description when considered in conjunction with the accompanying drawings, wherein like reference characters designate like parts throughout the several views, and wherein.

DETAILED DESCRIPTION OF THE PREFERRED EMBODIMENTS

Figure 1:
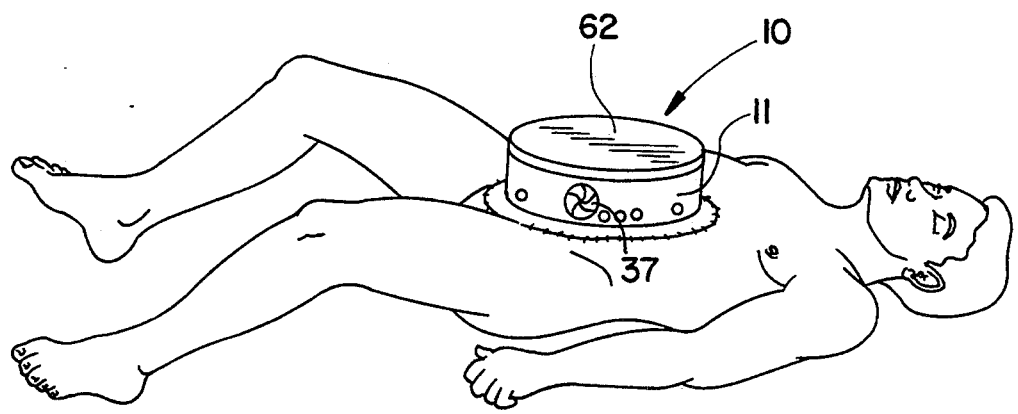
FIG. 1 is a top perspective view showing the apparatus of the invention in place on a patient, with a cover secured in place to close the top of the well formed by the cylindrical wall, and accessory devices removed, as might be the case when the patient is placed in an ICU with the apparatus in place for follow-up procedures.
Figure 2:
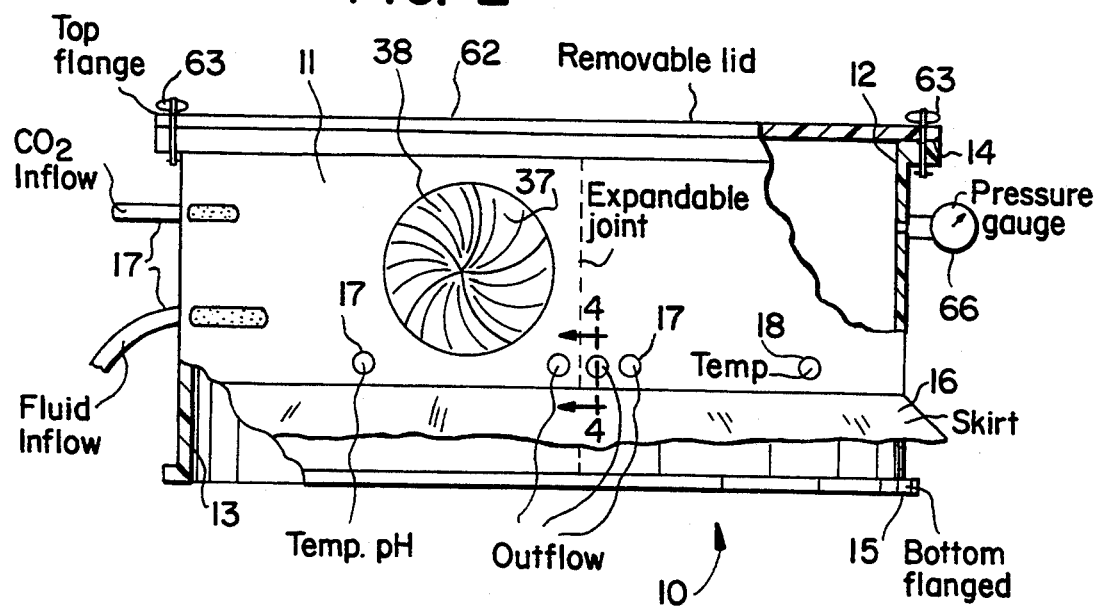
FIG. 2 is an enlarged view in side elevation of a form of the apparatus according to the invention, wherein a skirt on the base end of the cylinder is used to stitch the cylinder in place to the abdominal wall.
Figure 3:
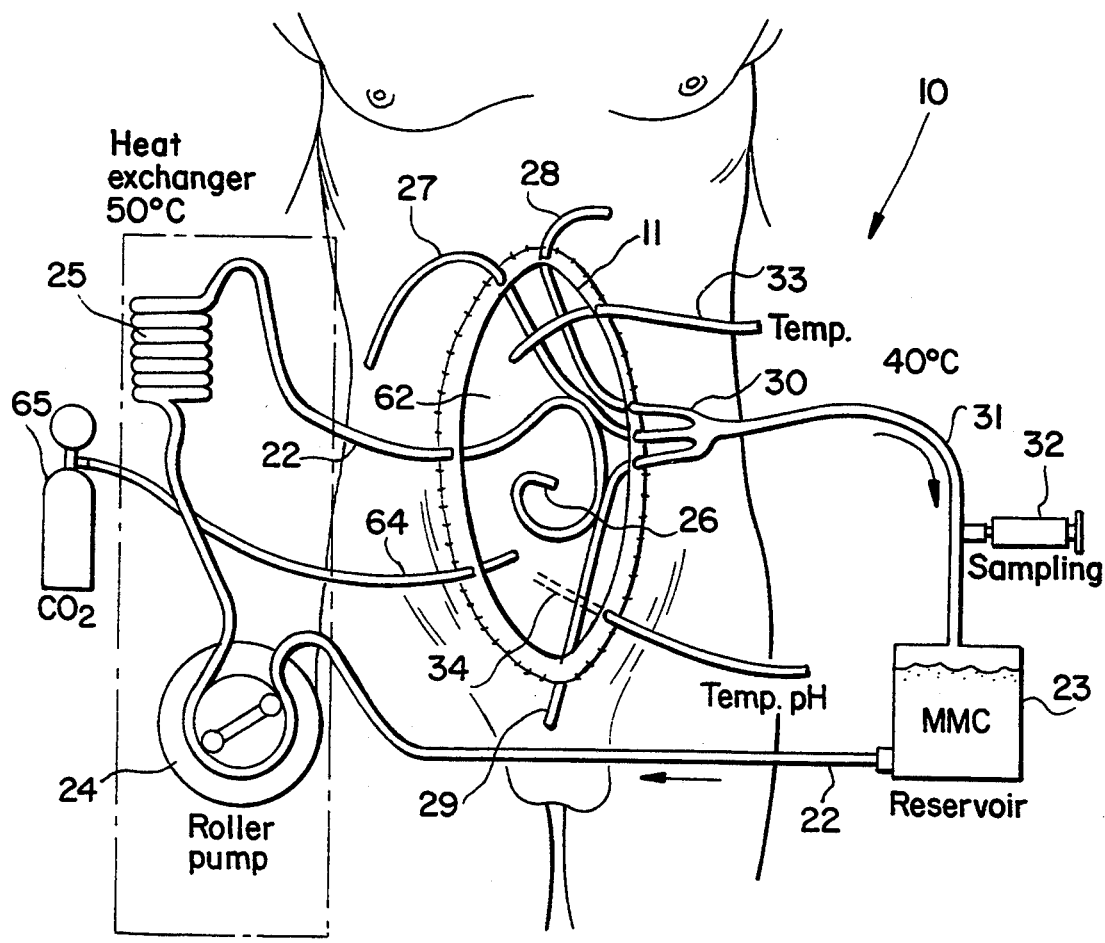
FIG. 3 is a partially schematic top plan of the apparatus of FIG. 2 shown stitched in place in an incision of the abdominal wall of a patient, with some of the accessory devices connected in operative relationship.

Referring more specifically to the drawings, a first form of abdomino-pelvic lavage apparatus is indicated generally at 10 in FIGS. 1–3. In this form of the invention, a cylindrical wall 11 with an oval shape in transverse cross-section has an open upper end 12 and an open base end 13. A relatively narrow upper annular flange 14 and a wider base flange 15 extend around the upper end and the base end, respectively, and a flexible annular skirt 16 is fixed and sealed at its inner marginal edge to an outer surface of the cylindrical wall at a location spaced a short distance above the base flange 15.

In use, the base end of the wall 11 is placed in the abdominal incision made by the surgeon, with the base flange positioned beneath the abdominal wall at the marginal edge of the incision and the skirt 16 positioned above the abdominal wall. The skirt is then sutured to the abdominal wall at the marginal edge of the incision to secure and seal the apparatus in the abdominal wall. Thus secured, the apparatus forms a well which enables the abdomino-pelvic cavity to be filled with lavage fluid. The surgeon also has free access to the abdomino-pelvic cavity so that he can manipulate intra-abdominal organs and stir the lavage fluid to maximize the effects of treatment. With this form of the invention, a water-tight well is formed by the wall and abdominal cavity, but the attachment between the base end of the wall and the abdominal wall is not air-tight.

A plurality of quick-connect couplings 17 are secured and sealed in openings or ports 18 formed through the wall at spaced locations around its circumference for connecting inflow and outflow tubes for the lavage fluid used to irrigate the abdominal cavity. The couplings may be of any suitable construction, and in the specific embodiment shown have a barbed end 20 on the outside of the wall and a tapered fitting 21 on the inside of the wall.

In the preferred embodiment, at least one inflow tube 22 is connected with a coupling 17 to supply lavage fluid from a reservoir 23 to the abdominal cavity. The lavage fluid is drawn from the reservoir and pumped into the abdominal cavity via a pump 24, and during hyperthermic treatment is heated in heat exchanger 25. The pump and heater may be of the type used in a heart-lung machine, or may be of any other type and construction suitable for the intended purpose. For instance, the pump may comprise a peristaltic type roller pump and the heater may comprise a coiled heat exchanger of conventional design. The heater is preferably operated so that the lavage fluid is heated to a maximum temperature of 50° C. The distal or discharge end 26 of the inflow tube may be positioned anywhere desired in the abdomino-pelvic cavity, and its position may be easily changed by the surgeon.

A plurality of drain or outflow tubes 27, 28 and 29 are positioned in the abdomino-pelvic cavity to drain the lavage fluid and any intra-abdominal contaminants carried thereby from the abdomino-pelvic cavity. Preferably, at least three such drain tubes are provided, with their distal, intake ends under the right hemidiaphragm, the left hemidiaphragm and the pelvis, respectively. These tubes are flexible but have sufficient stiffness to remain in place once positioned by the surgeon. They may be attached through a coupler 30 to a single drain tube 31 which leads to the reservoir 23. Particulate material, coagulants and the like may be removed from the fluid via a sump or filter, not shown, before return of the fluid to the patient.

A syringe 32 or other suitable device is connected with the drain tube 31 for drawing off a sample of the lavage fluid drained from the abdomino-pelvic cavity to enable the fluid to be analyzed so that the efficacy of the treatment can be determined.

Temperature probes 33 may also be inserted through selected ports 18 to measure the temperature of the lavage fluid in the abdomino-pelvic cavity during hyperthermic therapy. These probes may be of the type used as esophageal temperature probes, or may have any other design suitable for the purpose. Preferably, the temperature sensing device is placed in proximity with the distal, intake ends of the drains.

One or more probes 34 can also be provided to measure the pH of the lavage fluid, and additional detectors (not shown) can be provided to measure the glucose level or to collect other data, as desired.

A Geiger counter, indicated schematically at 35 may also be positioned over the abdomen to detect any leakage into the systemic circulation. Radioactive technetium, for example, can be used in conjunction with the lavage fluid to enable such leakage to be detected. A further Geiger counter, indicated schematically at 36, may be placed over the heart to enable the amount of any leakage to be documented in an online manner. By comparing simultaneous readings over the abdominal cavity and over the heart, the absorption of chemotherapy or other drugs can be estimated and a maximum dose delivered with the surgical event.

Figure 12:
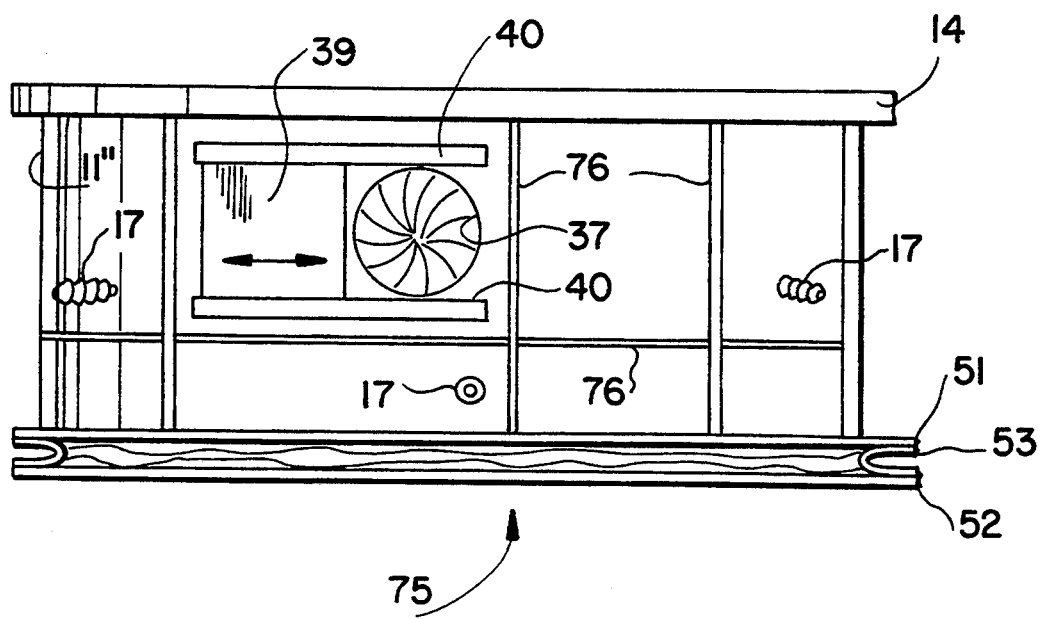
FIG. 12 is a somewhat schematic side view in elevation of a modification of the invention wherein the cylindrical wall of the apparatus is scored to define fracture lines to facilitate breaking up of the wall into smaller pieces for easier disposal.

To enable the surgeon to have free access to the abdomino-pelvic cavity during a lavage procedure, one or more gloved ports 37 are provided through the wall 11. These ports may be closed during pressurization of the abdomino-pelvic cavity by use of a manually opened and closed iris diaphragm 38 (FIG. 2) or other suitable closure, such as a sliding plate 39 held in a pair of channels 40 on the wall 11 (FIG. 12). By inserting his hands through these ports, the surgeon can manipulate intra-abdominal fluid to insure that all fibrinous accumulations are disbursed. This also permits manual "scrubbing" of the narrow margins of excisions, manipulate of all peritoneal crevices, and visual inspection of all bowel surfaces.

Figure 5:
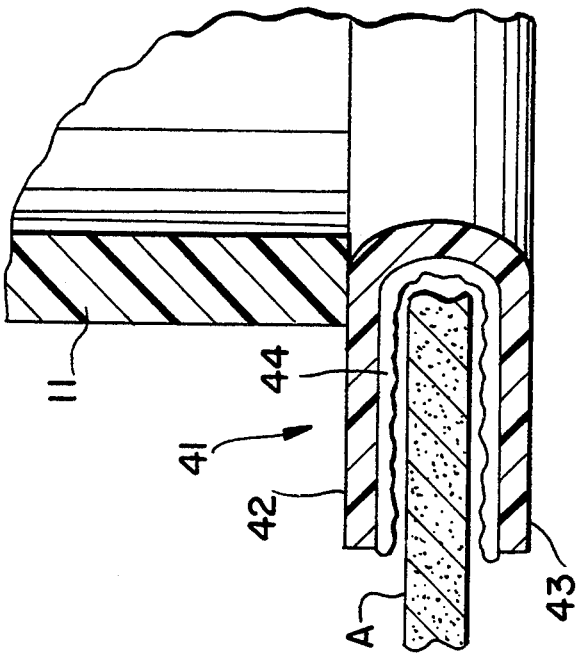
FIG. 5 is a greatly enlarged fragmentary sectional view of a modification of the invention, wherein spaced flanges are on the bottom of the wall, with an inflatable ring for securing and sealing the apparatus to the edges of an abdominal incision, with the ring shown deflated.
Figure 4:
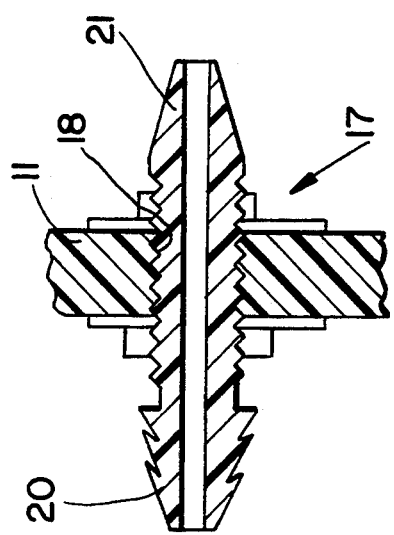
FIG. 4 is a greatly enlarged fragmentary sectional view of one of the coupling devices for connecting tubing through the cylindrical wall of the apparatus, taken along line 4—4 in FIG. 2.
Figure 6:
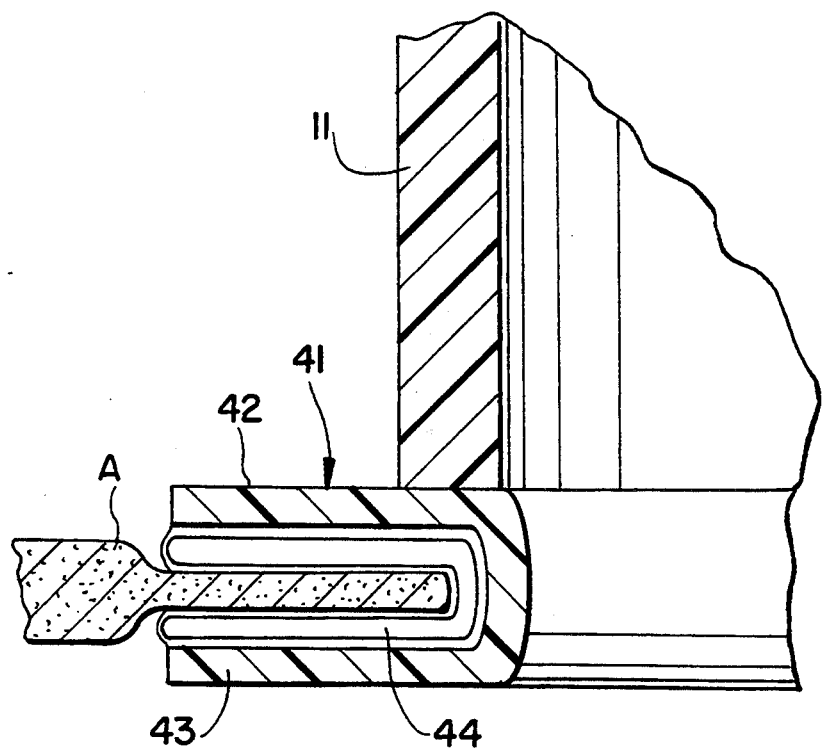
FIG. 6 is a view similar to FIG. 5, showing the ring inflated.

A modification of the invention is indicated at 41 in FIGS. 5 and 6. In this form of the invention, a member having essentially a U-shape in transverse cross-section is fixed to the base end of the wall 11, defining a pair of parallel, horizontally extending, spaced flanges 42 and 43 opening in a radially outward direction relative to the wall. An inflatable ring or bladder 44 is secured in the space between the flanges, so that in use the surgeon may place the edges of the incision made through the abdominal wall A between the flanges and inflate the bladder to grip the edges of the incision and effect and air and water-tight seal.

Figure 7:
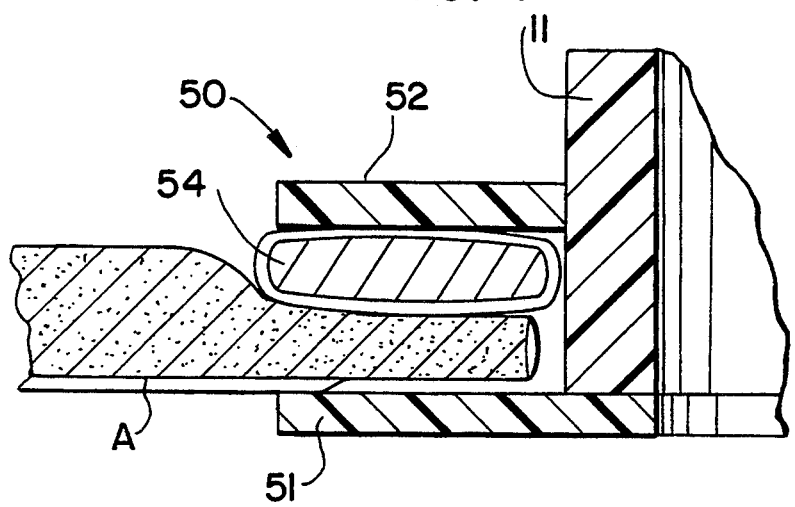
FIG. 7 is an enlarged fragmentary sectional view similar to FIG. 6, of a further modification utilizing a different form of spaced flanges and inflatable ring.

A variation of this form of the invention is indicated generally at 50 in FIG. 7, wherein a single annular flange 51 is secured on the base end of the wall 11 and a separate annular flange 52 is secured on the outer circumference of the wall spaced upwardly from the flange 53. An inflatable bladder 54 between the flanges may be inflated to grip the edges of the incision through the abdominal wall A and form an air and water-tight seal therewith.

Figure 9:
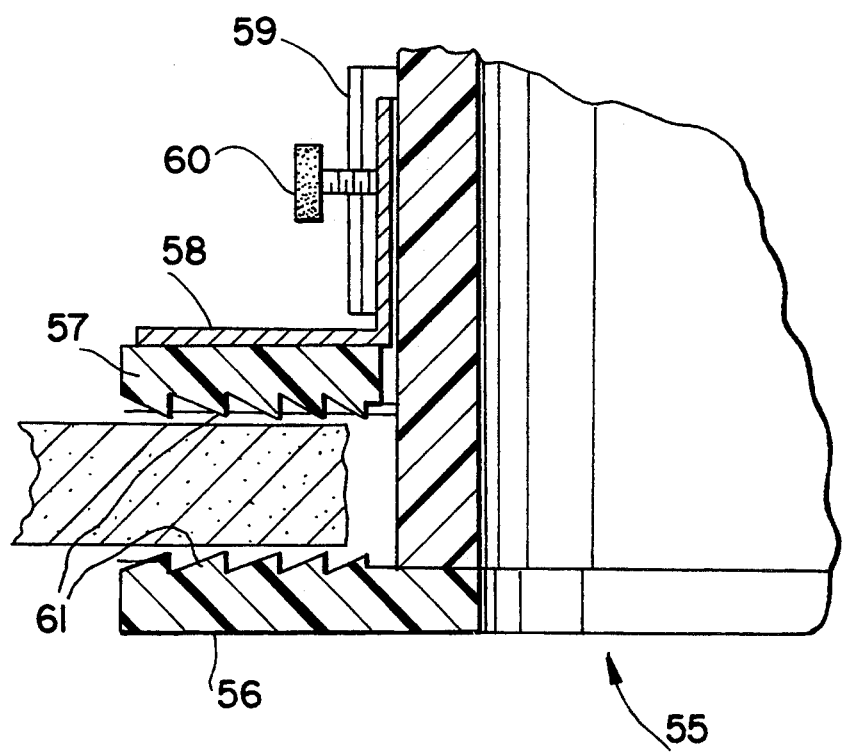
FIG. 9 is a greatly enlarged view in section, taken along line 9—9 in FIG. 8.
Figure 8:
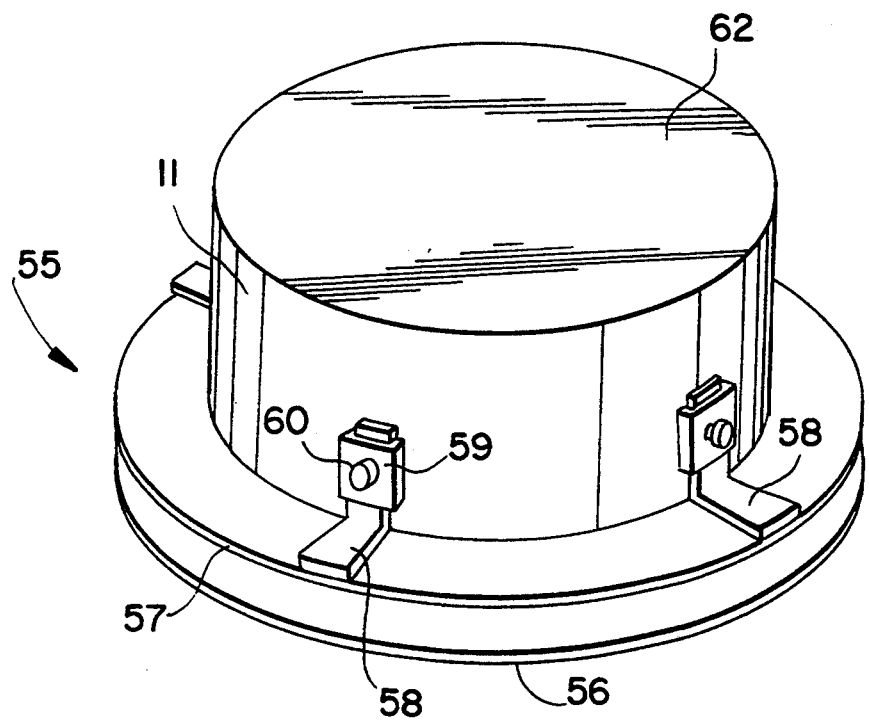
FIG. 8 is a top perspective view of another modification, wherein a movable compression plate is held by adjustable clamps to grip the edges of an abdominal incision between the plate and a fixed flange.

A further variation of the clamping flange on the base end of the wall is indicated generally at 55 in FIGS. 8 and 9. In this form of the invention, a radially outwardly directed base flange 56 is provided on the base end of the wall 11, and an annular clamping ring 57 is slidable on the outside of the wall in upwardly spaced relationship to the flange 56. A plurality of uniformly spaced clamps 58 are slidably mounted in opposed channels 59 on the outside of the wall, and are held in vertically adjusted positions by set screws 60. The facing surfaces of the base flange and clamping ring have roughened surfaces, such as the saw-tooth configuration shown at 61, for effecting a secure grip on the marginal edges of an abdominal incision placed between the flange and clamping ring and producing both an air and water-tight seal with the abdominal wall. In use, the base flange is placed beneath the edge of the incision and the clamping ring is then pressed down on top of the edge of the incision, after which the clamping screws are tightened to hold the clamping ring firmly in position.

A transparent, removable lid or cover 62 may be secured over the upper end of the cylindrical wall 11 by any suitable means, such as fasteners 63 extended through the flange 14, to seal the abdomino-pelvic cavity and interior of the wall from atmosphere. This enables the apparatus to be used in chemotherapy without exposing operating room personnel to chemotherapy aerosols. It also enables the abdomino-pelvic cavity and interior of the apparatus to be pressurized with a gas, such as $CO_2$. This pressure can be utilized to force any chemotherapy drug into surface tissue that is especially at risk. A pressure fitting 64 can be provided for supply of pressurized gas to the interior space of the apparatus from a source 65 of the pressurized gas, and a pressure gauge 66 can be attached to the wall to measure the pressure in the space.

By leaving the cover in place, the apparatus can be left in the incision and the patient can be returned to a surgical intensive care unit for follow-up examination and treatment. Repeated inspection and lavage of the abdominal cavity can be accomplished without return to the operating room. The lavage fluid may contain acid to lower pH, sugar to elevate glucose levels, antibiotics, chemotherapy and fibrinolytic agents. Examples of chemotherapy drugs which have been found effective in hyperthermic perfusion of the peritoneal cavity are cisplatin (CDDP) and mitomycin C (MMC).

Figure 10:
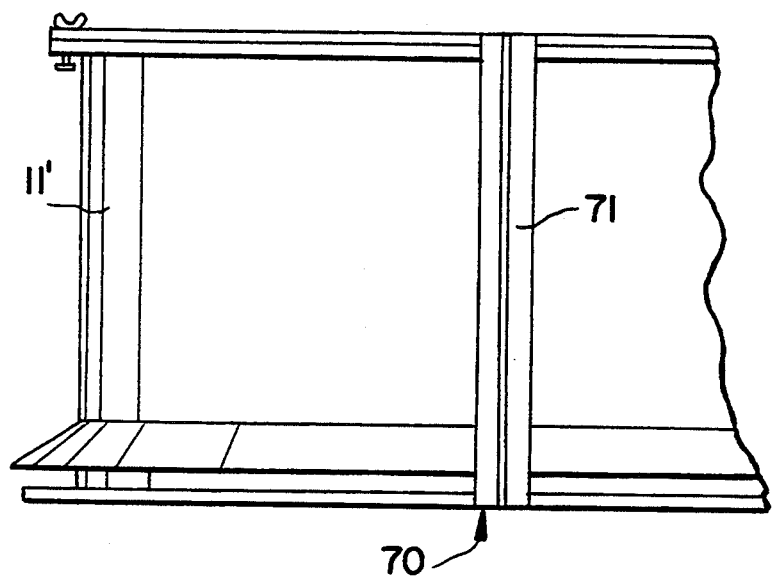
FIG. 10 is a somewhat schematic top plan view of a cylindrical wall in accordance with the invention, wherein the wall includes an expansible joint to enable adjustment of the apparatus to different size incisions.
Figure 11:
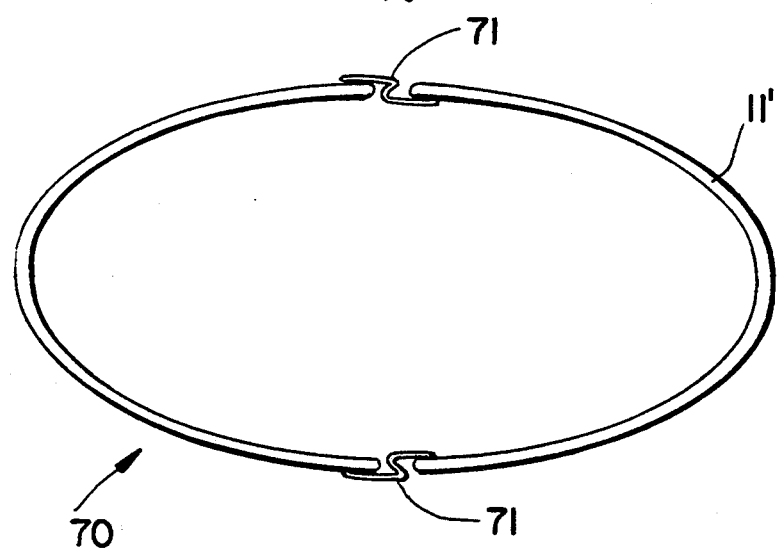
FIG. 11 is a fragmentary side view in elevation of the expansible cylinder of FIG. 10.

In FIGS. 10 and 11 a further modification is indicated generally at 70. In this form of the invention, the wall 11' is split vertically on one or both sides and an expansible joint or seam 71 is connected between the adjoining edges of the wall. This enables the apparatus to be adjusted or accommodated to different size incisions.

FIG. 12 shows yet another variation of the invention at 75, wherein score lines 76 are provided at spaced intervals on the wall 11'', defining fracture lines to facilitate breaking of the wall into smaller pieces for disposal. After use, the surgeon or other operating room personnel may simply place the wall on its side and step on it to cause it to fracture along the score lines into small pieces for easy disposal. If desired, the wall may first be placed in a plastic bag and then stepped on to facilitate disposal of the parts.

Figure 13:
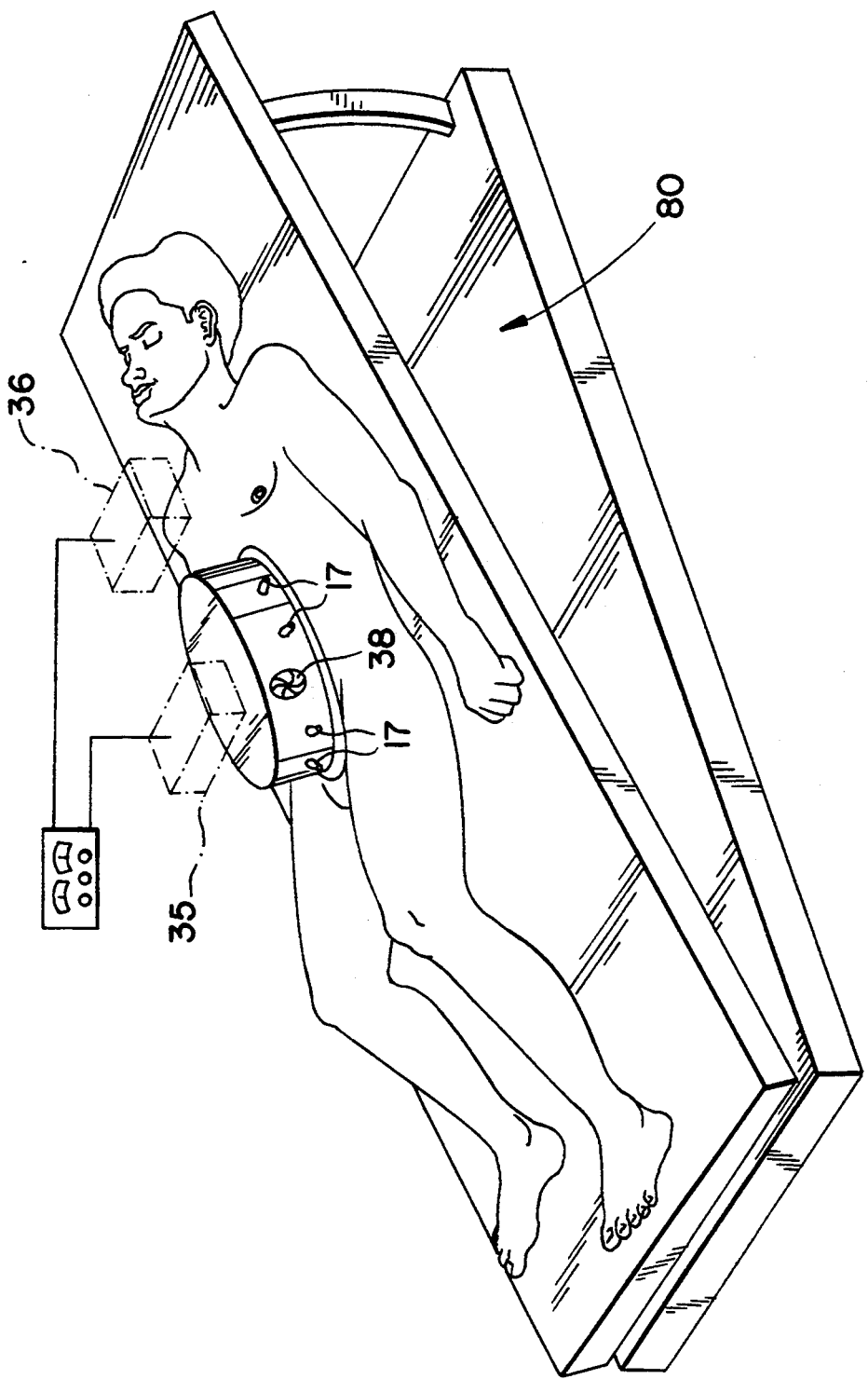
FIG. 13 is a schematic perspective view showing the operating table being tilted to incline the patient for flooding a particular portion of the abdomino-pelvic cavity.

Referring to FIG. 13, a procedure is illustrated in which the operating room table may be tipped, as shown at 80, to incline the patient to form a "puddle" or pool of fluid containing drugs in the pelvic area for concentrating an extra high dosage of drugs in that area for treatment of particular portions of the abdomino-pelvic cavity which are at increased risk for cancer recurrence. This is true, for example, in a patient with rectal cancer with pelvic recurrence. In this instance, the surgeon may wish to treat a particular portion of the abdominal cavity with an especially high dosage of chemotherapy. It may further be desired to place this chemotherapy under pressure. When the operating room table is adjusted, as shown, to incline the patient's body so that the pelvis is lower, the pelvic area can be filled by gravity with high concentration of multi-drug chemotherapy. A temperature probe, inflow tube and outflow drain (not shown) are placed in this "puddle" of chemotherapy. In this special clinical situation, the inflow and outflow catheters are placed in a single portion of the abdomen, such as the pelvis. While the pelvis is filled and refilled with heated chemotherapy, pressure is applied in order to force the chemotherapy into the tissues which are at great risk. After this "boost" dose of chemotherapy to the area at great risk, additional lavage fluid is added and the remainder of the abdominal cavity at less risk is treated with a lower dose of chemotherapy, heat and pressure.

The invention thus provides a simple and effective apparatus for lavaging the abdomino-pelvic cavity, and especially to such an apparatus which enables the surgeon free access to the abdomino-pelvic cavity during the lavage process and which permits accurate monitoring and control of temperature and pressure within the abdomino-pelvic cavity during treatment, particularly during hyperthermic and hyperbaric peritoneal lavage for the treatment of peritoneal dissemination in intra-abdominal cancers and other related clinical situations.

What is claimed is:

1. An abdomino-pelvic lavage apparatus for attachment in an incision formed through the abdominal wall of a patient to facilitate treatment during an abdomino-pelvic lavage procedure performed on the patient, comprising:

a cylindrical wall impervious to water and air having an upper end and a base end;

means on the base end of the wall for securing and sealing the wall in an incision formed through the abdominal wall;

means for supplying lavage fluid through the wall to the abdomino-pelvic cavity and draining the fluid from the cavity; and at least one sealed gloved port formed through the cylindrical wall through which a surgeon can insert his hands to gain free access to the abdomino-pelvic cavity during a lavage procedure, said cylindrical wall forming a well with the abdominal wall for containing the lavage fluid during a lavage procedure.

2. An abdomino-pelvic lavage apparatus as claimed in claim 1, wherein:

a removable cover is secured and sealed over the upper end of the cylindrical wall to enclose the well formed thereby, forming a barrier to aerosols so that chemotherapy can be used without exposing operating room personnel to chemotherapy aerosols, and the apparatus may be left in place on a patient who may then be returned to an intensive care unit for follow-up examinations and repeated lavage procedures without necessitating use of the operating room.

3. An abdomino-pelvic lavage apparatus as claimed in claim 2, wherein:

a source of pressurized gas is connected through the cylindrical wall to pressurize the well and abdomino-pelvic cavity to force drugs into tissues being treated.

4. An abdomino-pelvic lavage apparatus as claimed in claim 1, wherein:

said means on the base end of the cylindrical wall for securing and sealing the wall in an incision comprises a pair of opposed, spaced apart, horizontal flanges on the base end of the cylindrical wall for receiving between them the abdominal wall at the edge of an incision formed through the abdominal wall; and an inflatable ring is between the flanges for exerting clamping pressure on the abdominal wall at the edge of the incision to secure and seal the cylindrical wall to the abdominal wall.

5. An abdomino-pelvic lavage apparatus as claimed in claim 1, wherein:

said means for supplying lavage fluid to the abdomino-pelvic cavity and draining it therefrom includes a pump means to circulate the lavage fluid from a source, through the abdomino-pelvic cavity and back to the source, and a heater means to heat the lavage fluid up to approximately 50° C. during use of the apparatus in hyperthermic peritoneal perfusion.

6. An abdomino-pelvic lavage apparatus as claimed in claim 5, wherein:

a heart-lung machine is used as said pump means and heater means.

7. An abdomino-pelvic lavage apparatus as claimed in claim 5, wherein:

there is at least one inflow tube connected through the cylindrical wall for admitting lavage fluid to the abdomino-pelvic cavity, and at least one drain tube connected through the cylindrical wall for draining lavage fluid from the abdomino-pelvic cavity.

8. An abdomino-pelvic lavage apparatus as claimed in claim 7, wherein:

there are three drain tubes extended into the abdomino-pelvic cavity of a patient, with the distal intake end of one drain tube disposed beneath the right hemidiaphragm of the patient, the distal intake end of a second drain tube disposed beneath the left hemidiaphragm of the patient, and the distal intake end of a third drain tube disposed in the pelvis of the patient.

9. An abdomino-pelvic lavage apparatus as claimed in claim 8, wherein:

a temperature sensor is positioned in proximity with the intake end of each drain tube to measure the temperature of the lavage fluid within the abdomino-pelvic cavity, said temperature sensors being connected with leads extending through the cylindrical wall.

10. An abdomino-pelvic lavage apparatus as claimed in claim 9, wherein:

a removable cover is secured and sealed over the upper end of the cylindrical wall to enclose the well formed thereby, forming a barrier to aerosols so that chemotherapy can be used without exposing operating room personnel to chemotherapy aerosols, and the apparatus may be left in place on a patient who may then be returned to an intensive care unit for follow-up examinations and repeated lavage procedures without necessitating use of the operating room.

11. An abdomino-pelvic lavage apparatus as claimed in claim 10, wherein:

a source of pressurized gas is connected through the cylindrical wall to pressurize the well and abdomino-pelvic cavity to force drugs into tissues being treated.

12. An abdomino-pelvic lavage apparatus as claimed in claim 5, wherein:

a removable cover is secured and sealed over the upper end of the cylindrical wall to enclose the well formed thereby, forming a barrier to aerosols so that chemotherapy can be used without exposing operating room personnel to chemotherapy aerosols, and the apparatus may be left in place on a patient who may then be returned to an intensive care unit for follow-up examinations and repeated lavage procedures without necessitating repeated use of the operating room.

13. An abdomino-pelvic lavage apparatus as claimed in claim 12, wherein:

said cylindrical wall is made of a synthetic plastic material and is disposable after use, said wall being scored at predetermined intervals to define a plurality of fracture lines so that the wall may be broken into a plurality of smaller pieces to facilitate disposal.

14. An abdomino-pelvic lavage apparatus as claimed in claim 13, wherein:

an expansible section is provided in said cylindrical wall so that the diameter of the wall may be adjusted to fit different size incisions.

15. An abdomino-pelvic lavage apparatus as claimed in claim 14, wherein:

said expansible section comprises at least one section extending the length of the cylindrical wall, said section comprising a deformable S-shaped pleated joint which may be stretched out and compressed.

16. An abdomino-pelvic lavage apparatus as claimed in claim 1, wherein:

said cylindrical wall is made of synthetic plastic material and is disposable after use, said wall being scored at predetermined intervals to define a plurality of fracture lines so that the wall may be broken into a plurality of smaller pieces to facilitate disposal.

17. An abdomino-pelvic lavage apparatus as claimed in claim 16, wherein:

a removable cover is secured and sealed over the upper end of the cylindrical wall to enclose the well formed thereby, forming a barrier to aerosols so that chemotherapy can be used without exposing operating room personnel to chemotherapy aerosols, and the apparatus may be left in place on a patient who may then be returned to an intensive care unit for follow-up examinations and repeated lavage procedures without necessitating use of the operating room.

18. An abdomino-pelvic lavage apparatus as claimed in claim 17, wherein:

a source of pressurized gas is connected through the cylindrical wall to pressurize the well and abdomino-pelvic cavity to force drugs into tissues being treated and to cause increased drug concentration at the peritoneal surface.

19. An abdomino-pelvic lavage apparatus as claimed in claim 18, wherein:

said means on the base end of the cylindrical wall for securing and sealing the wall in an incision comprises a pair of opposed, spaced apart, horizontal flanges on the base end of the cylindrical wall for receiving between them the abdominal wall at the edge of an incision formed through the abdominal wall; and an inflatable ring is between the flanges for exerting clamping pressure on the abdominal wall at the edge of the incision to secure and seal the cylindrical wall to the abdominal wall.

20. An abdomino-pelvic lavage apparatus as claimed in claim 1, wherein:

an expansible section is provided in said cylindrical wall so that the diameter of the wall may be adjusted to fit different size incisions.

21. An abdomino-pelvic lavage apparatus as claimed in claim 20, wherein:

said expansible section comprises at least one section extending the length of the cylindrical wall, said section comprising a deformable S-shaped joint which may be stretched out and compressed.

22. An abdomino-pelvic lavage apparatus as claimed in claim 1, wherein:

an annular skirt having an inner marginal edge and an outer marginal edge is attached at its inner edge to an outer circumferential surface of the cylindrical wall and is stitched at its outer marginal edge to the abdominal wall around an incision formed through the abdominal wall to secure the apparatus in place in the incision.

23. A method for lavaging the abdomino-pelvic cavity, comprising the steps of:

making an incision through the abdominal wall of the abdomen:

securing one end of a generally cylindrical wall in the incision formed through the abdominal wall so that the cylindrical wall extends upwardly from the abdominal wall to form a well with the abdomino-pelvic cavity for containing lavage fluid;

introducing lavage fluid through the cylindrical wall into the abdomino-pelvic cavity for irrigating intra-abdominal tissues;

providing gloved openings in the cylindrical wall through which a surgeon may insert his hands for free access to the abdomino-pelvic cavity for manipulation of the lavage fluid and intra-abdominal tissues, scrubbing of the narrow margins of excisions, disbursal of fibrinous accumulations and visual inspection of all bowel surfaces; and draining the lavage fluid from the abdomino-pelvic cavity to flush fibrinous debris and other intra-abdominal contaminants from the cavity.

24. A method as claimed in claim 23, including the steps of:

adding drugs to the lavage fluid for treatment of diseases, infection and the like in the abdomino-pelvic cavity.

25. A method as claimed in claim 24, including the steps of:

heating the lavage fluid to a predetermined temperature before it is introduced into the abdomino-pelvic cavity to increase the toxicity of the drugs to the disease being treated.

26. A method as claimed in claim 24, including the steps of:

pressurizing the lavage fluid and drugs in the well and abdomino-pelvic cavity to force the drugs into the tissue being treated and create a high concentration of drug in tissue at the peritoneal surface.

27. A method as claimed in claim 26, including the steps of:

heating the lavage fluid to a predetermined temperature before it is introduced into the abdomino-pelvic cavity to increase the toxicity of the drugs to the disease being treated.

28. A method as claimed in claim 24, including the steps of:

tilting or inclining the patient being treated so that the patient's head is higher than the patient's feet to form a pool or puddle of lavage fluid in the pelvic cavity of the patient for treatment of a particular portion of the abdomino-pelvic cavity.

29. A method as claimed in claim 28, including the steps of:

increasing the concentration of drugs in the lavage fluid so that the particular portion being treated will be subjected to a higher concentration of drugs.

* * * * *